US010115576B2

(12) United States Patent
Geromanos et al.

(10) Patent No.: US 10,115,576 B2
(45) Date of Patent: Oct. 30, 2018

(54) METHOD AND AN APPARATUS FOR ANALYZING A COMPLEX SAMPLE (71) Applicant: Waters Technologies Corporation, Milford, MA (US)

(72) Inventors: Scott J. Geromanos, Middletown, NJ (US); Marc V. Gorenstein, Needham, MA (US); Daniel Golick, Newtown, MA (US); Steven J. Ciavarini, Natick, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 572 days.

(21) Appl. No.: 14/563,022

(22) Filed: Dec. 8, 2014

(65) Prior Publication Data
US 2015/0170892 A1 Jun. 18, 2015

Related U.S. Application Data (60) Provisional application No. 61/914,990, filed on Dec. 12, 2013.

(51) Int. Cl.
G01N 30/86 (2006.01)
H01J 49/00 (2006.01)
(Continued)

(52) U.S. Cl.
CPC .......... H01J 49/004 (2013.01); G01N 27/622 (2013.01); G01N 30/72 (2013.01);
(Continued)

(58) Field of Classification Search
CPC ................ H01J 49/0086; H01J 49/009; G01N 2030/0095; G01N 30/8689
See application file for complete search history.

(56) References Cited

U.S. PATENT DOCUMENTS 9,111,735 B1 8/2015 Nikolaev et al.
2003/0001084 A1 1/2003 Bateman et al.
(Continued)

FOREIGN PATENT DOCUMENTS

WO 2005/114930 A2 12/2005

OTHER PUBLICATIONS

Geromanos, S. J. et al., "Simulating and validating proteomics data and search results," Proteomics, 2011, v. 11, pp. 1189-1211.
(Continued)

Primary Examiner — Cheung Lee (57) ABSTRACT

A method of analyzing a complex sample includes performing a sequential chromatographic-IMS-MS analysis of a sample to obtain a plurality of experimental mass spectra having isotopic clusters, wherein each spectrum of the plurality of spectra is associated with a chromatographic retention time and an ion-mobility drift time. The method also includes calculating a model isotopic cluster of a precursor or product ion associated with a candidate compound in the sample, in correspondence to the natural isotopic-abundance ratios of elements composing the compound. The method further includes comparing peaks of the model isotopic cluster to corresponding peaks of an isotopic cluster of one of the experimental mass spectra to extract one or more saturated or interfered peaks of the experimental isotopic cluster, wherein at least one of the peaks of the experimental isotopic cluster is un-saturated and un-interfered.

19 Claims, 5 Drawing Sheets (51) Int. Cl.
*G01N 27/62* (2006.01)
*G01N 30/72* (2006.01)
(52) U.S. Cl.
CPC ..... *G01N 30/7233* (2013.01); *G01N 30/8631* (2013.01); *G01N 30/8679* (2013.01); *H01J 49/0036* (2013.01)

(56) References Cited

U.S. PATENT DOCUMENTS

2004/0108452 A1* 6/2004 Graber ............... G01N 33/6803
250/281
2013/0338935 A1   12/2013 Watanabe et al.
2014/0299762 A1   10/2014 Mukaibatake

OTHER PUBLICATIONS

Geromanos, S. J. et al., "Using ion purity scores for enhancing quantitative accuracy and precision in complex proteomics samples," Anal Bioanal Chem, publ online Jun. 19, 2012, DOI 10.1007/s00216-012-6197-y; in print Sep. 2012, v. 404, pp. 1127-1139.
Thalassinos, K., et al., "Design and application of a data-independent precursor and product ion repository," J. Am. Mass Spectrom., 2012, v. 23, pp. 1818-1820.
United Kingdom Search and Examination Report for Application No. 1421942.2, dated Dec. 21, 2015.

* cited by examiner

210: chromatography device
220: ion-mobility spectrometry module
222: drift tube
230: mass spectrometry
232: oa-TOF mass analyzer
240: a data processing unit

METHOD AND AN APPARATUS FOR ANALYZING A COMPLEX SAMPLE

CROSS-REFERENCE TO RELATED APPLICATION

This application claims priority to and benefit of U.S. Provisional Application No. 61/914,990 filed Dec. 12, 2013, the contents and teachings of which are incorporated herein by reference in their entirety.

TECHNICAL FIELD

This disclosure relates generally to analysis of a complex sample and, more particularly, to quantitation of compounds in a complex sample by liquid chromatography (LC), ion-mobility spectrometry (IMS) and mass spectrometry (MS).

BACKGROUND

MS coupled with LC is a common approach to quantifying compounds in a sample. The quantitation is typically performed by first separating compounds by LC to generate a sequence of chromatograms, each associated with a retention time (RT) window; next, ionizing and detecting the separated compounds by MS to produce a plurality of mass spectra having ion peaks; then, using a peak area or a sum area of all peaks within a mass window, associated with a target compound, to infer quantitative information about the compound, assuming there is a correlation between the peak area and the compound concentration.

This approach, however, faces difficult challenges in quantifying a target compound in a complex sample, for it is based conceptually upon two assumptions: first, all ion peaks used in quantitation are associated with a target compound; second, all ion peaks used in quantitation are shaped and positioned as theoretically predicted. However, these assumptions do not hold in quantifying compounds intertwined in a complex sample, because as the complexity (or/and dynamic range) of a sample increases, the chance of multiple compounds co-eluting from LC in a same RT window is also magnified, resulting in mass spectra, where ions from different compounds occupy a same mass-to-charge-ratio (m/z) space and interfere with each other. Moreover, as the complexity of a sample increases, the number of high-abundance compounds in the sample proportionally increases as well, which can saturate a detector and corrupt linearity of detector response, given that there will always exist an instrumental limit of detection. Accordingly, a signal profile is no longer correlated with the quantity of the compounds, as their concentration increases beyond a level that saturates a detector.

The term "complex sample," as used herein, refers to a sample that contains a multitude of naturally occurring or man-made biological components, such as proteins, peptides, metabolites, lipids, antibodies in serum, or mixtures thereof.

SUMMARY

Some embodiments arise, in part, from the realization that the quantitative accuracy and effective dynamic range of mass analysis of a complex sample can be enhanced by acquiring data on a chromatographic-IMS-MS system, producing a sequence of experimental mass spectra having isotopic clusters associated with a target compound; calculating a model isotopic cluster in correspondence to an experimental isotopic cluster; and comparing the calculated model cluster to the experimental cluster, wherein at least one un-saturated and un-interfered peak of the experimental isotopic cluster is used to extract saturated or interfered peaks from the experimental isotopic cluster of the target compound.

The term "model isotopic cluster," as used herein, refers to a group of isotopic molecules or isotopic compositions, pertaining to a compound, having masses and relative intensities that are calculated based on the natural isotopic-abundance ratios of elements composing the compound. The term "experimental isotopic cluster," as used herein, refers to a group of detected ions, which has the same elemental composition but different isotopic compositions, and which is observed from an experimental mass spectrum.

The terms "molecule," "compound" and "ion," as used herein, are exchangeable, in the context of an elemental composition they all share.

The terms "isotopic peak," "isotopic ion," "isotope," "mass peak," "ion peak" and "ion" will be understood by one of ordinary skill in the art to refer to a mass peak of a mass spectrum.

Some embodiments exploit knowledge of compounds composed of elements having naturally occurring isotopes having multiple molecular masses due to natural abundance-ratios of the isotopes. Consequently, such a compound, when analyzed by MS, forms a series of isotopic ions enveloped in one or more isotopic clusters. The disclosure takes advantage of a chromatographic-IMS-MS system that combines multi-dimensional separation capacity with high mass resolving power and thus can produce simplified experimental mass spectra that have fewer and better resolved isotopic peaks distributed in one or more isotopic clusters. Such simplified experimental mass spectra lay out a ground, upon which quantitative analysis of a complex sample is performed.

Some embodiments entail determination of a model isotopic cluster, associated with a compound, by a calculation based on the natural isotopic-abundance ratios of the elements that compose the compound. Such a model isotopic cluster provides model intensity ratios between any pair of isotopic peaks of the compound. Some embodiments further use a model isotopic cluster and a single un-saturated and un-interfered isotopic peak in a corresponding experimental isotopic cluster to infer the correct intensities of saturated or interfered isotopic peaks in the same experimental isotopic cluster, these embodiments can improve quantitative accuracy across an extensive dynamic range.

One embodiment provides a method of analyzing a complex sample, which includes performing a sequential chromatographic-IMS-MS analysis of a sample to obtain a plurality of experimental mass spectra having isotopic clusters. Each spectrum of the plurality of spectra is associated with a chromatographic retention time and an ion-mobility drift time. The method also includes calculating a model isotopic cluster of a precursor or product ion associated with a candidate compound in the sample, in correspondence to the natural isotopic-abundance ratios of elements composing the compound. The method further includes comparing peaks of the model isotopic cluster to corresponding peaks of an isotopic cluster of one of the experimental mass spectra to extract one or more saturated or interfered peaks of the experimental isotopic cluster. At least one of the peaks of the experimental isotopic cluster is un-saturated and un-interfered.

In some implementations, the sample is a biological sample, including, foe example, proteins, peptides, metabolites, lipids, or the mixtures thereof.

In some implementations, the experimental mass spectra comprise at least one precursor or product ion spectrum, or both thereof, associated with the candidate compound.

In some implementations, the method includes determining values associated with peak shape. Values associated with peak shape can include, for example, full-width-at-half-maximum height (FWHM).

In some implementations, the method further includes establishing a filter for each of the peaks in each of the experimental isotopic clusters. The filter is a criterion to judge the quality of a mass peak and established based on the values associated with peak shape, a predetermined instrumental resolution and a tolerance value, and the instrumental resolution comprises a mass resolution.

In some implementations, the method further includes identifying one or more saturated or interfered peaks and any un-saturated and un-interfered peak in each of the experimental isotopic clusters, based on the filter for each of the peaks in each of the experimental isotopic cluster.

In some implementations, wherein identifying repeats for each of the peaks in each of the experimental isotopic clusters, first through the experimental isotopic clusters of a precursor ion, then through the experimental isotopic clusters of a product ion, until an un-saturated and un-interfered peak is identified.

In some implementations, calculating the model isotopic cluster comprises computing the number, masses and relative intensities of the isotopic compositions of the candidate compound, based on the natural isotopic-abundance ratios of the elements composing the compound.

In some implementations, calculating the model isotopic cluster includes referencing one or more library spectra to find a match between an experimental isotopic cluster and an isotopic cluster in one spectrum of the library spectra, and the library spectra are produced from statistical analysis of repetitive identifications of compounds same as the candidate compound.

In some implementations, comparing includes correcting intensities of the saturated or interfered peaks, based on the model isotopic cluster and un-saturated and un-interfered peak(s) in the experimental isotopic cluster.

In some implementations, comparing further includes reconstructing the experimental isotopic cluster, based on the peaks of correct and/or corrected intensities, thereby achieving quantitative accuracy across a wide dynamic range on both saturated and interfered with isotope clusters.

Another embodiment features a system, which includes: a chromatography module for separation of a sample comprising compounds of interest; an IMS module configured to receive the sample separated by the chromatography module and further separate the received sample; a MS module configured to perform mass analysis on the further separated sample; and a data processing unit, in communication with the MS module, comprising one or more processors and a plurality of executable programs, which, when executed by one of the processors, implements the method described above.

In some implementations, the chromatography module is a liquid chromatography (LC) module.

In some implementations, the IMS module is embedded in the MS module, and a mass analyzer of the MS module has mass resolving power in a range of about 20,000 to about 100,000 FWHM.

In some cases, the mass spectrometry module comprises an orthogonal acceleration time-of-flight mass analyzer.

Other implementations, features and advantages will be apparent in view of the description, drawings and claims.

BRIEF DESCRIPTION OF THE DRAWINGS

In the drawings, same or like reference characters and numbers generally refer to same or like elements throughout different views. Also, the drawings are not necessarily to scale.

FIGS. 4A and 4B are graphs of two mass spectra.

DETAILED DESCRIPTION

Some illustrative implementations will now be described with respect to FIGS. 1-4. In view of this description, claims and figures, modifications and alterations to these implementations, and alternative embodiments, will be apparent to one of ordinary skill.

Figure 1:
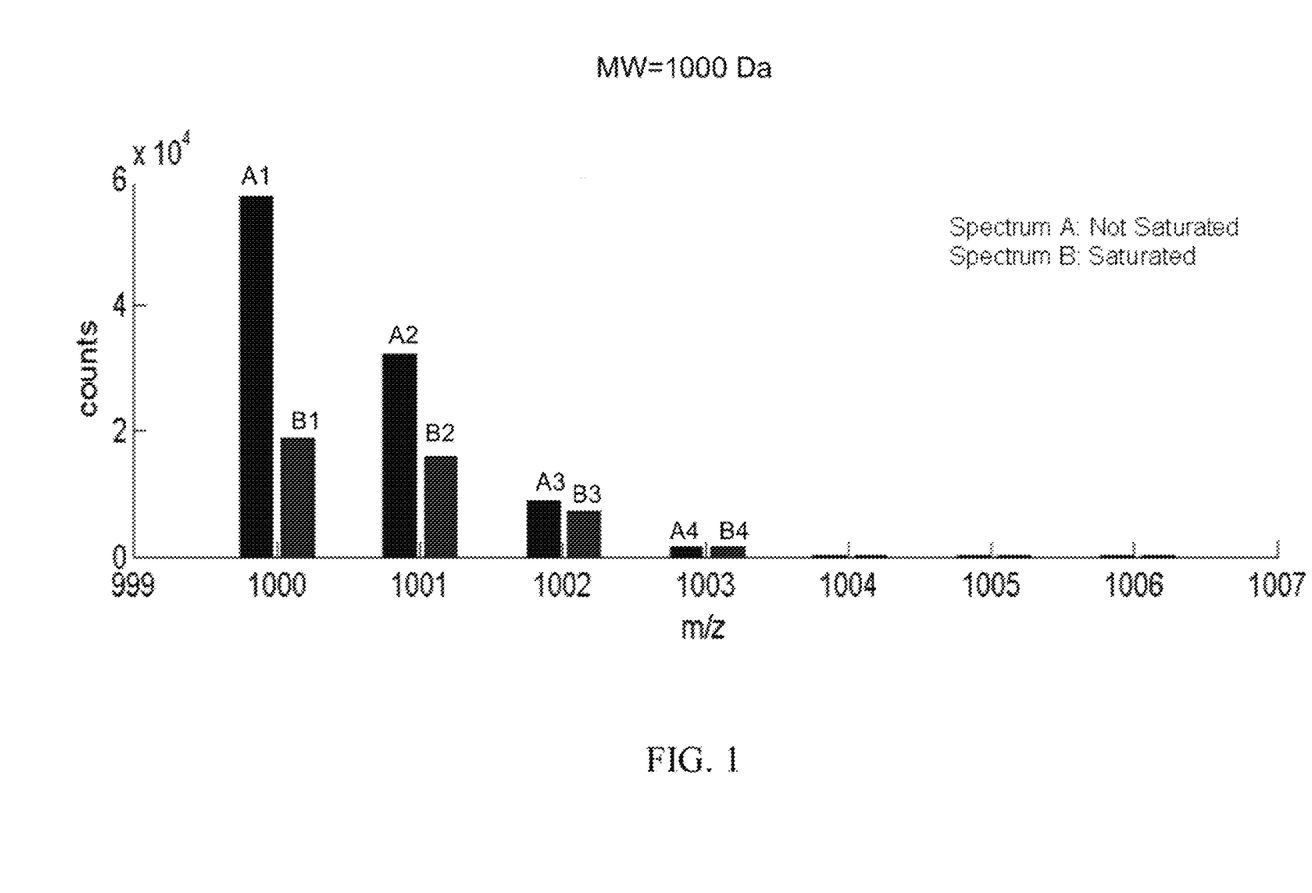
FIG. 1 shows two simulated mass spectra A, B of a same compound, where A is from an un-saturated detector, whereas B is affected by detector saturation.

FIG. 1 shows two simulated mass spectra A, B, both associated with a compound of a molecular weight of 1000 Dalton (Da). Spectrum A contains isotopic peaks from an un-saturated detector, while spectrum B contains isotopic peaks affected by detector saturation. As can be seen from spectrum B, the most intense peaks and intensity ratios between the peaks are most affected by detector saturation.

Figure 2:
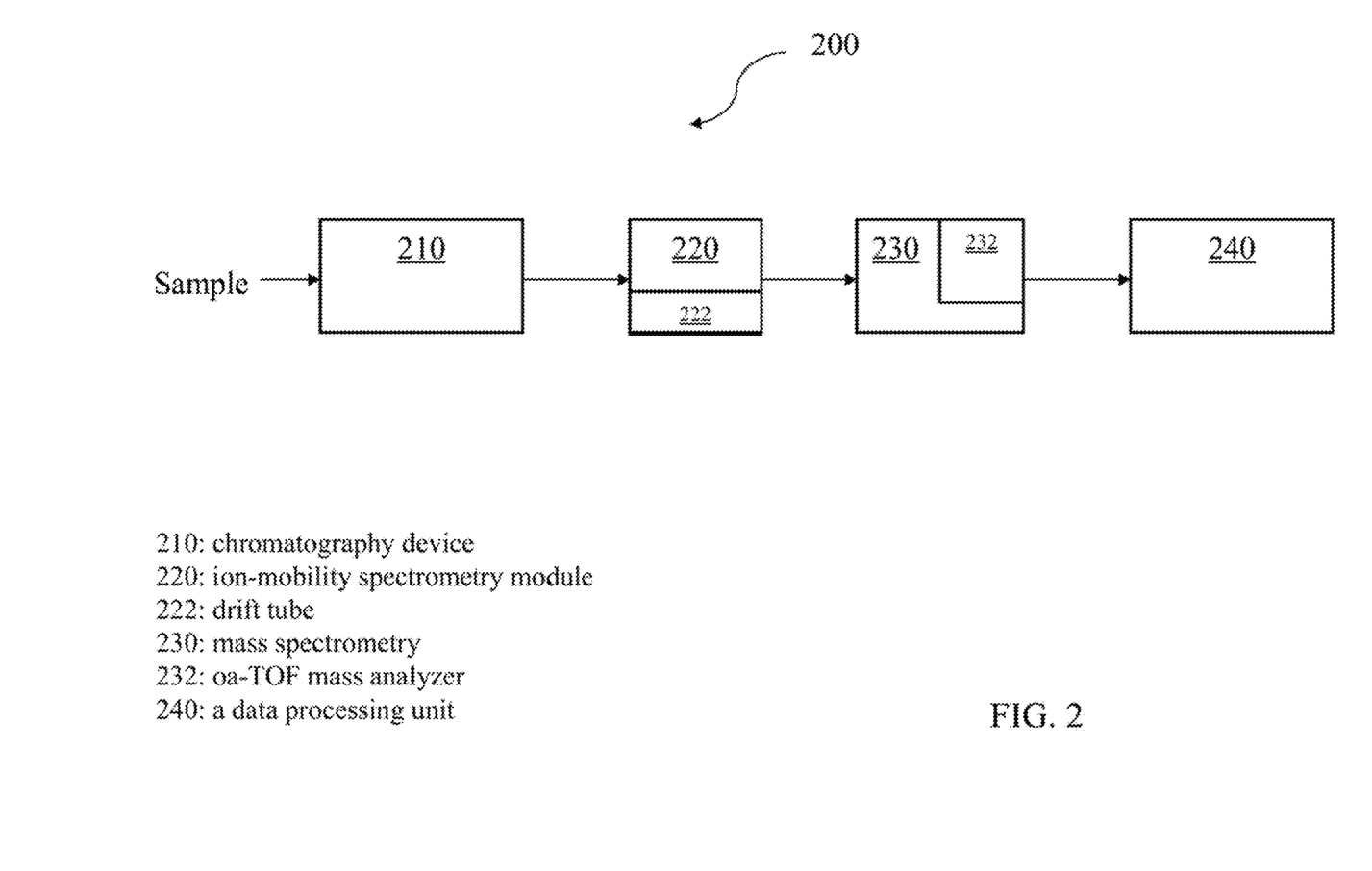
FIG. 2 is a schematic overview of a chromatographic-IMS-MS system, in accordance with one embodiment of the invention.

FIG. 2 is a schematic overview of a system 200 for analysis, such as for identification and quantitation of a complex sample, which includes a chromatography module 210, an IMS module 220, a MS module 230, and a data processing unit 240.

In some implementations, the chromatography module 210 is a LC module, where a mixture of compounds is carried in a liquid mobile phase and flows through a chromatography column packed with a stationary phase to be separated. The compounds are separated due to their different affinities for the mobile and stationary phase. LC is powerful in separating compounds of distinctive physico-chemical properties, for example, compounds of different polarities or different transport capabilities across the mobile phase. The separation generates a sequence of chromatograms, each designated by a RT window associated with one or more compounds. The chromatography module 210 can have any suitable configuration, e.g., one- or two-dimensional configuration, or be at any suitable scale, e.g., micro- or nano-scale, as will be understood by one having ordinary skills in chromatography. An example of a chromatography module, with which some embodiments of the invention are suitably implemented, is a nanoACQUITY UPLC® system, available from Waters Corporation, Milford, Mass.

The IMS module 220 separates compounds, based on their mobilities or drift times (DT). In preferred implementations, the IMS module 220 is embedded in the MS module 230. Compounds are first ionized and then travel through the drift tube 222 included in the IMS module 220. The drift tube 222 has an applied electric field and is filled with a drift gas optionally flowing in a direction opposite to the ion motion. An ion's mobility is determined by its m/z and its "collisional cross-section," which is a function of the ion's shape and size. In general, the greater the collisional cross-section is, the longer the DT the ion takes. IMS provides an additional dimension of separation to a sample and can differentiate some compounds that are hardly distinguishable by LC, e.g., the compounds of similar physicochemical properties and co-eluting from LC in a same RT window. This additional dimension of separation minimizes effects of ion interferences in complex samples.

A number of different forms of IMS can be used. In some embodiments, the IMS module 220 includes a drift tube having a number of guard rings that can be interconnected by equivalent valued resistors and connected to a direct current (DC) voltage source that generates a linear DC voltage gradient along the drift tube. In other embodiments, the IMS module 220 may include a Field Asymmetric IMS. In further embodiments, the IMS module 220 includes a number of plate electrodes, each having an aperture through which ions are transmitted. An example of an IMS module, with which some embodiments of the invention are suitably implemented, is described in US Patent Publication No. 2003/01084 to Bateman et al., published on Jan. 2, 2003.

The MS module 230 performs mass analysis on the compounds separated by the chromatography module 210 and further by the IMS module 220, and produces a plurality of experimental mass spectra having isotopic clusters associated with a candidate compound, wherein each of the experimental mass spectra is associated with a chromatographic RT and an ion-mobility DT. In some implementations, the MS module 230 includes an orthogonal acceleration time-of-flight (oa-TOF) mass analyzer having a mass resolving power in a range of about 20,000 to about 100,000 FWHM. The MS module 230 can have any suitable configurations, as can be understood by one having ordinary skill in the mass-spectrometry arts. An example of such MS module is a SYNAPT™ High Definition MS system, available from Waters Corporation, Milford, Mass.

Figure 3:
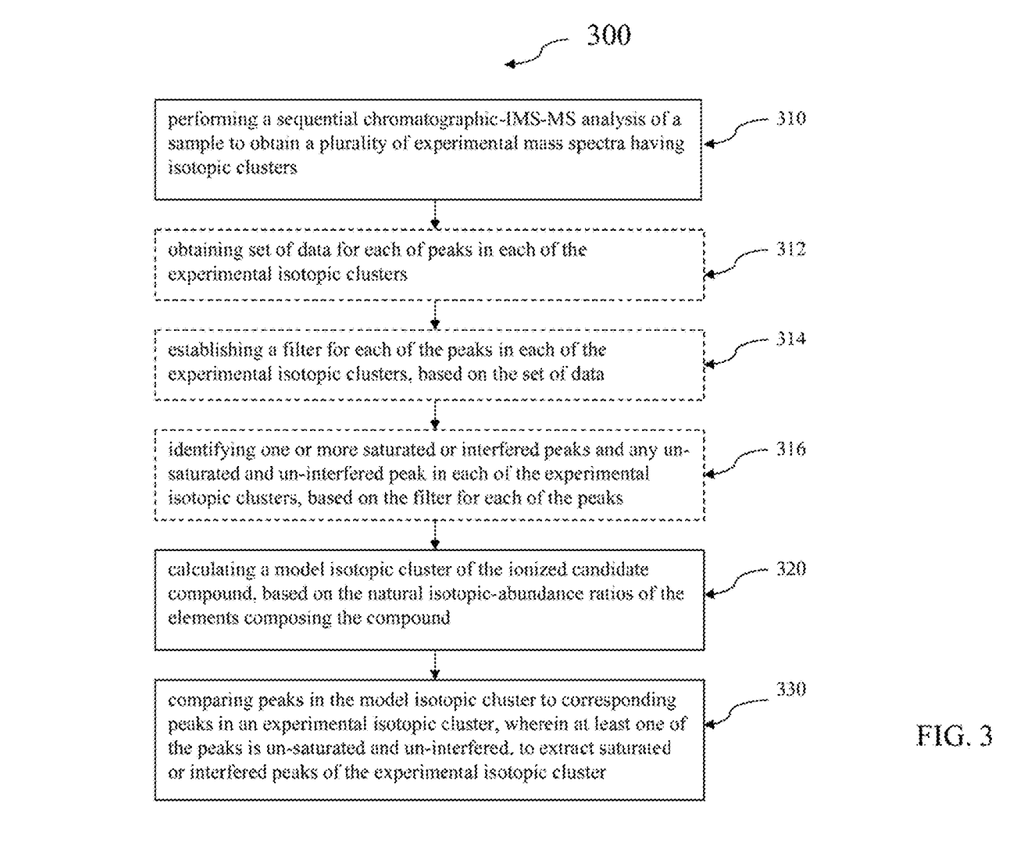
FIG. 3 is a flow diagram of a method for analyzing or, more particularly, quantifying a complex sample, in accordance with another embodiment of the invention.

The data processing unit 240, in communication with the MS module 230, receives mass signals from the MS module 230 and performs mass-spectrometric analysis of the sample, based on the received signals. The data processing unit 240 can include commonly used computing systems. Examples of well known computing systems include, but are not limited to, personal computers, server computers, handheld or laptop devices, multiprocessor systems, microprocessor-based systems, minicomputers, mainframe computers and the like as known in the art. The data processing unit 240 has a plurality of executable programs, which, when executed by one of the processors, implements a method, the description of which immediately follows FIG. 3 is a flow diagram of a method 300 for analysis of a complex sample. The method includes performing (310) a sequential chromatographic-IMS-MS analysis of a sample to obtain a plurality of experimental mass spectra having isotopic clusters. Each spectrum of the plurality of spectra is associated with a chromatographic RT and an ion-mobility DT. The method also includes calculating (320) a model isotopic cluster of a precursor or product ion associated with a candidate compound in the sample, in correspondence to the natural isotopic-abundance ratios of elements that compose the compound. The method further includes comparing (330) peaks of the model isotopic cluster to peaks of a corresponding experimental isotopic cluster to extract one or more saturated or interfered peaks of the experimental isotopic cluster. At least one peak in the experimental isotopic cluster is un-saturated and un-interfered, which can be used to infer the correct intensities of saturated or interfered peaks of the same experimental cluster, based on the model isotopic cluster.

In most implementations, the method is used for quantitative analysis of a compound in a complex sample, for example, analysis of abundance or change in relative abundance of the compound from, e.g., a control sample.

All naturally occurring elements, e.g., carbon, hydrogen, etc., exist as mixtures of isotopes, and, consequently, any compound composed of naturally occurring elements has multiple molecular masses that correspond to the different isotopes and to the natural isotopic-abundance ratios of each element. Accordingly, such a compound, when ionized, exists as a plurality of isotopic ions distributed in one or more isotopic clusters and the intensity ratio between any pair of isotopic ions in an isotopic cluster is, in theory, proportional to the natural isotopic-abundance ratio of the elements composing the compound. The method 300 makes use of this natural phenomenon in mass-spectrometric quantitation of a complex sample.

In most implementations, performing (310) includes collecting data from the sample on a system, which includes a chromatography module, an IMS module and a MS module, to produce a sequence of raw mass spectra, associated with the candidate compound, which have series of isotopic ions distributed in one or more isotopic clusters, depending on the number of charge states of the isotopic ions. Each spectrum of the raw mass spectra is associated with a chromatographic RT and an ion-mobility DT. An example of such a system is the system 200 shown in FIG. 2, which combines multi-dimensional separation capacity with high mass resolving power and produces simplified mass spectra that have fewer and better resolved peaks. Additionally, performing (310) includes processing the raw mass spectra, for example, including baseline detection, smoothing and noise reduction. Processing produces a plurality of resolved experimental mass spectra, each containing a series of isotopic peaks distributed in one or more isotopic clusters, each designated with a charge state.

In some implementations, the method 300 includes obtaining (312), from the experimental mass spectra, a set of data for each peak in each of the experimental isotopic clusters. The set of data includes a m/z, values associated with the peak shape, such as peak height, peak area and FWHM, and RT and DT, associated with one of the mass spectra where the peak resides. A detailed description in how to obtain the data, for example, is provided in an article published on *Proteomics,* 2011, 11, 1-23, by Scott Geromanos et al.

In some implementations, the method 300 further include establishing (314), based on the set of data obtained in the step (312), a filter for each of the mass peaks in each of the experimental isotopic clusters. The filter is a criterion to judge the quality of a mass peak, e.g., how well a peak is measured and whether a peak is saturated or interfered. The filter can be established through expected values associated with the peak shape, e.g., an expected FWHM, which can be calculated based on a known or predetermined instrumental mass resolution and a tolerance value. For example, if a MS module has a predetermined mass resolution of 20,000 for a peak having a centered mass of 2000 Da, then the expected FWHM of the peak can be calculated by dividing the centered mass by the mass resolution, which is 0.1 Da. This expected FWHM can then serve as a filter for judging a mass peak, together with a tolerance value. For example, if the measured FWHM of a mass peak is greater than the expected value, plus or minus a tolerance value, then the peak is considered saturated or interfered. Similarly, a filter for a chromatographic peak and for a drift peak can be calculated, based on the expected respective instrument performance. In some implementations, a filter for an observed mass peak is established by incorporating the filters of a corresponding chromatographic and drift peak, and a weighted average of the filters is used to qualify an observed mass peak. A detailed description on how to establish such a filter for each mass peak, for example, is provided in *Anal. Bioanal. Chem.*, 2012, DOI 10.1007/s00216-012-6197-y, by Scott Geromanos et al.

Additionally, the method 300 includes identifying (316) one or more saturated or interfered ion peaks in one of the experimental isotopic clusters. At least one of the peaks is un-saturated and un-interfered, based on the established filter for each of the peaks in the experimental isotopic cluster. If the FWHM of a peak does not match its expected FWHM within a set tolerance, then the peak is identified as a saturated or interfered peak, and otherwise the peak is un-saturated and un-interfered. The step of identifying (316) optionally repeats for each ion peak in each of the experimental isotopic clusters, first through the peaks of a precursor ion, then the peaks of a product ion, until an un-saturated and un-interfered peak is identified, if at least one ion peak in one of the experimental isotopic clusters is un-saturated and un-interfered. With the simplified and well resolved experimental mass spectra produced, e.g., from the system 200, corrupted and uncorrupted peaks can be identified effectively, since peaks and interference events in each of experimental isotopic clusters are greatly reduced, so that any distortion imposed on a peak can be relatively easily recognized.

In some implementations, calculating (320) a model isotopic cluster of the ionized candidate compound involves computing the number, masses and relative intensities of isotopic molecules or isotopic compositions pertaining to the compound, based on the elemental isotopes and their abundance ratios. For example, for bio-molecules, most of the isotopic composition variation arises from carbon, where the natural abundance of $^{13}C$ is about 1.1% of $^{12}C$. Such information can be used to calculate the relative abundances of different isotopic compositions of a bio-molecule. The relative intensities of the ions of an isotopic cluster of such a bio-molecule can be estimated from formula 1

$$I_n = \binom{N}{n} p^n (1-p)^{N-n} \quad (1)$$

where N is the total number of carbon atoms in a molecule, n is the number of $^{13}C$ isotopes, p is the natural abundance of $^{13}C$, and $I_n$ is the relative intensity of each $^{13}C$ isotope in the molecule.

Calculating (320) provides a theoretical isotopic distribution of a compound, and such a model isotopic cluster or theoretical isotopic distribution a model can be used to predict intensity ratios of the isotopic peaks of an observed isotopic cluster of the ionized compound.

In some implementations, calculating (320) includes referencing library spectra or database spectra showing isotopic patterns or clusters of compounds having physicochemical properties similar to that of the candidate compound. Such library spectra or database spectra are normally obtained from statistical analysis of replicate spectra or repetitive identifications of compounds same as or similar to the candidate compound. Once a match between an experimental isotopic cluster and an isotopic cluster in one spectrum of the library spectra is found, then the isotopic cluster from the library spectrum can be utilized as a model isotopic cluster corresponding to the experimental isotopic cluster. A detailed description of how to calculate a model isotopic cluster by referencing library spectra, for example, is provided in *J. Am. Soc. Mass Spectrum*, 2012, DOI: 10.1007/s13361-012-0416-9, by Konstantinos Thalassinos et al.

The method 300 further includes comparing (330) peaks in the model isotopic cluster to corresponding peaks in an experimental isotopic cluster. At least one of the peaks is un-saturated and un-interfered, to extract one or more saturated or interfered peaks in the experimental isotopic cluster Comparing (330) optionally includes inferring the correct intensities of the saturated or interfered peaks, based the model isotopic cluster and the at least one un-saturated and un-interfered peak in the experimental isotopic cluster. For example, if ion A1 is identified as un-saturated and un-interfered peak and A2 as a saturated or interfered one, and if, based on the calculated model isotopic cluster, the abundance ratio of ion A1 to ion A2 is 1:10, then the correct intensity of ion A2 can be inferred by multiplying the intensity of ion A1 by 10. In the same manner, the correct intensities of other saturated or interfered peaks in the same experimental isotopic cluster can also be inferred. Comparing (330) optionally includes reconstructing the entire experimental isotopic cluster, thereby supporting quantitative accuracy across a wide dynamic range.

Figure 4A:
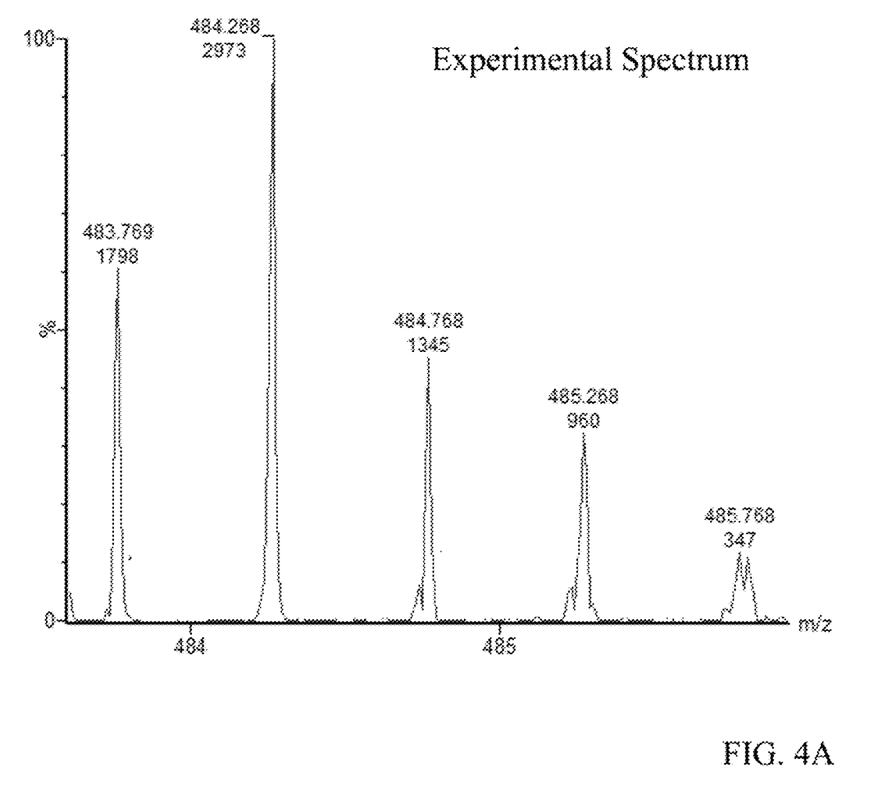
FIG. 4A is an experimental spectrum having two isotopic clusters overlapped and FIG. B shows the two clusters resolved by applying the method, as illustrated in FIG. 3.
Figure 4B:
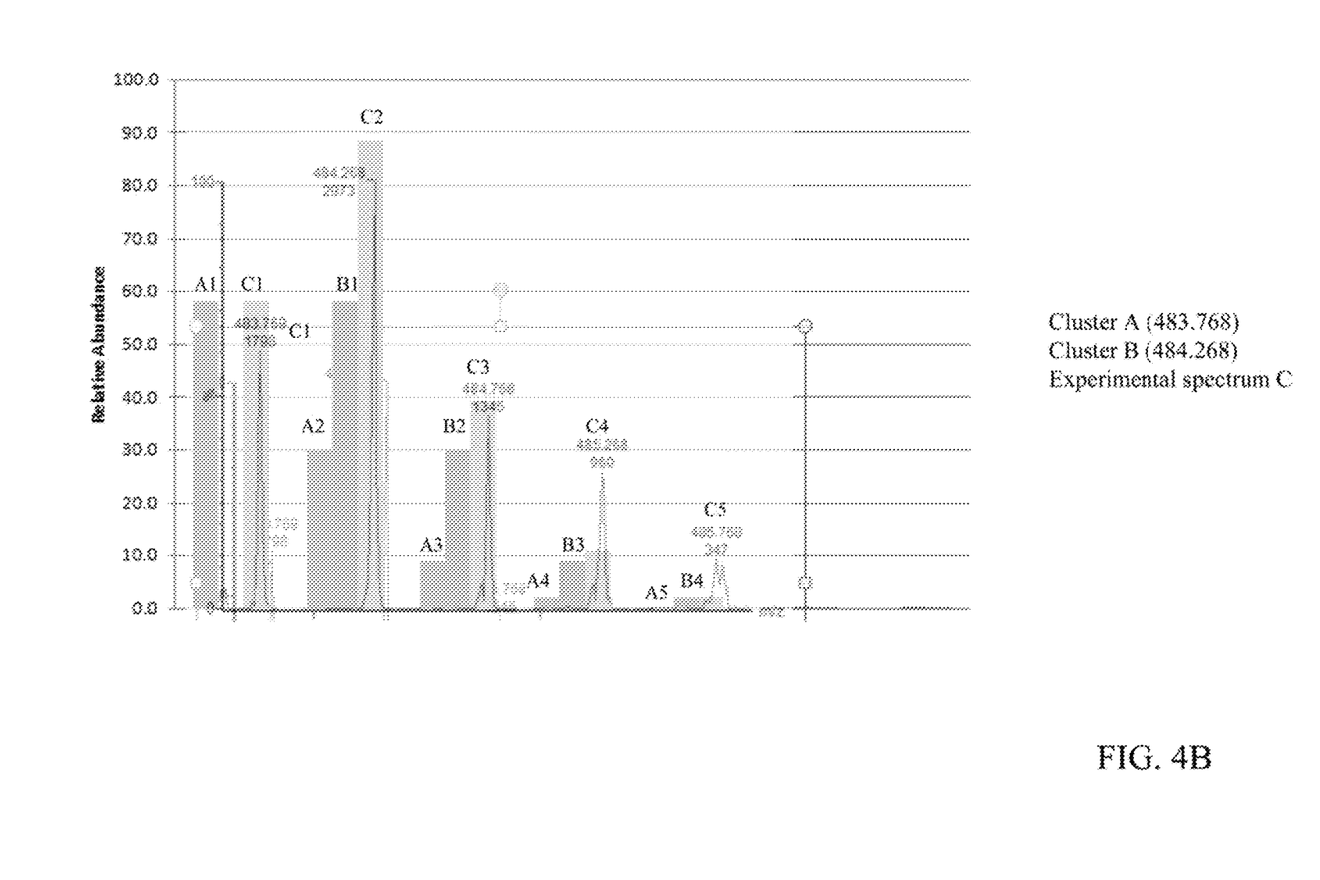

FIGS. 4A and 4B are graphs of two mass spectra. FIG. 4A is an experimental spectrum containing two isotopic clusters A, B that are overlapped or interfered with each other. A has a first isotopic peak with a m/z value of 483.768 and B has a first isotopic peak with a m/z value of 484.268. FIG. 4B shows that the two clusters A, B are resolved, by applying the method illustrated in FIG. 3, and overlaid with the experimental spectrum of FIG. 4A.

Although a number of implementations have been described above, other modifications, variations and implementations are possible in light of the foregoing teaching. For example, though, as described above, a sample is separated by a chromatographic module coupled with an IMS module, before being introduced to a MS module, a sample can be introduced directly onto a mass spectrometer by infusion, e.g., through a syringe pump, if the sample is not complicated.

For example, though, as described above, a corrupted peak, either saturated or interfered, can be identified through a filter that is established, based on the expected values associated with the peak shape, alternatively, a corrupted peak can be recognized through pattern matching, i.e., by directly matching an experimental isotopic cluster, where the peak resides, against a theoretical or expected one, associated with a same compound.

Accordingly, the invention is to be defined not by the preceding illustrative description but instead by the scope of the following claims.

What is claimed is:

1. A computer-implemented method of analyzing a complex sample, comprising:
generating, via a sequential chromatographic-IMS-MS apparatus, a separated sample by separating the complex sample based on a chromatographic retention time via a chromatography module and an ion-mobility drift time via an ion-mobility spectrometry (IMS) module;

performing, via a mass spectrometry (MS) module of the sequential chromatographic-IMS-MS apparatus, mass analysis of the separated sample to generate a plurality of experimental mass spectra having isotopic clusters, wherein each spectrum of the plurality of spectra is associated with the chromatographic retention time and the ion-mobility drift time; and resolving, via a data processing unit operably coupled to the sequential chromatographic-IMS-MS apparatus, one or more saturated or interfered peaks of the experimental isotopic cluster by:

calculating a model isotopic cluster of a precursor or product ion associated with a candidate compound in the sample, in correspondence to the natural isotopic-abundance ratios of elements composing the compound; and comparing peaks of the model isotopic cluster to corresponding peaks of an isotopic cluster of one of the experimental mass spectra to extract one or more saturated or interfered peaks of the experimental isotopic cluster, wherein the peaks of the experimental isotopic cluster comprise at least one un-saturated and un-interfered peak.

2. The method of claim 1, wherein the sample is a biological sample comprising proteins, peptides, metabolites, lipids, or mixtures thereof.

3. The method of claim 1, wherein the experimental mass spectra comprise at least one precursor or product ion spectrum, or both thereof, associated with the candidate compound.

4. The method of claim 1, wherein performing further comprises processing raw spectral data for charge-state deconvolution.

5. The method of claim 1, wherein resolving further comprises identifying one or more of the extracted saturated or interfered peaks and any un-saturated and un-interfered peak in each of the experimental isotopic clusters, in response to a peak-shape parameter for each of the peaks in each of the experimental isotopic clusters.

6. The method of claim 5 wherein resolving further comprises comprising repeating the step of identifying for each of the peaks in each of the experimental isotopic clusters, first through the experimental isotopic clusters of a precursor ion, then through the experimental isotopic clusters of a product ion, until an un-saturated and un-interfered peak is identified.

7. The method of claim 1, wherein calculating the model isotopic cluster comprises referencing one or more library spectra to find a match between an isotopic cluster of the experimental mass spectra and an isotopic cluster in one spectrum of the library spectra.

8. The method of claim 7, wherein the library spectra are associated with repetitive identifications of compounds that are the same as the candidate compound.

9. The method of claim 1, wherein comparing comprises inferring correct intensities of the saturated or interfered peaks, based on the model isotopic cluster and un-saturated and on un-interfered peak in the experimental isotopic cluster.

10. The method of claim 9, wherein comparing further comprises reconstructing the experimental isotopic cluster with the peaks of inferred correct intensities.

11. The method of claim 1, wherein resolving further comprises generating at least one peak of corrected intensity by correcting an intensity of at least a portion of the one or more saturated or interfered peaks based on the model isotopic cluster and the at least one un-saturated and un-interfered peak.

12. The method of claim 11, wherein resolving further comprises generating a resolved mass spectrum comprising the experimental mass spectrum overlaid with the at least one peak of corrected intensity.

13. A system for analyzing a complex sample, comprising:

a mass spectrometry apparatus comprising:

a chromatography module for separation of the complex sample comprising compounds of interest based on a chromatographic retention time;

an ion-mobility spectrometry module configured to:
receive the complex sample separated by the chromatography module; and
generate a separated sample by separating the received sample based on an ion-mobility drift time;

a mass spectrometry module configured to perform mass analysis on the separated sample to generate a plurality of experimental mass spectra having isotopic clusters, wherein each spectrum of the plurality of spectra is associated with the chromatographic retention time and the ion-mobility drift time; and a data processing unit, in communication with the mass spectrometry module, comprising one or more processors and a plurality of executable programs, which, when executed by one of the one or more processors, causes the data processing unit to:

resolve one or more saturated or interfered peaks of the experimental isotopic cluster by:
calculating a model isotopic cluster of a precursor or product ion associated with a candidate compound in the sample, in correspondence to the natural isotopic-abundance ratios of elements composing the compound; and
comparing peaks of the model isotopic cluster to corresponding peaks of an isotopic cluster of one of the experimental mass spectra to extract one or more saturated or interfered peaks of the experimental isotopic cluster, wherein at least one of the peaks of the experimental isotopic cluster is un-saturated and un-interfered.

14. The system of claim 13, wherein the chromatography module is a liquid chromatography module.

15. The system of claim 13, wherein the ion-mobility spectrometry module is embedded in the mass spectrometry module.

16. The system of claim 13, wherein the mass spectrometry module comprises an orthogonal acceleration time-of-flight mass analyzer.

17. The system of claim 16, wherein the mass analyzer has mass resolving power in a range of about 20,000 to about 100,000 FWHM.

18. The method of claim 1, wherein resolving further comprises identifying a saturated or interfered peak based on a peak shape value associated with the saturated or interfered peak being outside of a tolerance value.

19. The method of claim 18, the peak shape value comprising a full-width-at-half-maximum (FWHM) value.

* * * * *